United States Patent
Gandini et al.

(10) Patent No.: US 6,548,073 B2
(45) Date of Patent: *Apr. 15, 2003

(54) TWO-PHASE COSMETIC COMPOSITION

(75) Inventors: Luciana Gandini, São Paulo (BR); Claudia Leo, São Paulo (BR); Elizabete Fernandes Vicentini Rosin, São Paulo (BR); Sandra Regina De Almeida, Santo Andre (BR)

(73) Assignee: Indústria e Comércio de Cosmeticos Natura Ltda., Itapecerica da Serra (BR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/437,399

(22) Filed: Nov. 10, 1999

(65) Prior Publication Data
US 2002/0068074 A1 Jun. 6, 2002

(30) Foreign Application Priority Data
Nov. 10, 1998 (BR) ............................................. 9804596

(51) Int. Cl.⁷ ........................... A61K 7/00; A01N 25/00
(52) U.S. Cl. ...................... 424/401; 514/937; 514/941
(58) Field of Search ................................ 424/401, 450, 424/405; 514/937, 941

(56) References Cited

U.S. PATENT DOCUMENTS

| 5,468,496 A | * | 11/1995 | Touzan et al. | 424/401 |
| 5,733,572 A | * | 3/1998 | Unger et al. | 424/450 |
| 5,871,758 A | * | 2/1999 | Nagy et al. | 424/401 |
| 5,980,925 A | * | 11/1999 | Jampani et al. | 424/405 |

FOREIGN PATENT DOCUMENTS

| GB | 2 206 048 | * 12/1988 |
| GB | 2206048 | * 12/1988 |

* cited by examiner

Primary Examiner—Thurman K. Page
Assistant Examiner—Blessing Fubara
(74) Attorney, Agent, or Firm—Smith, Gambrell & Russell

(57) ABSTRACT

The present invention refers to a two-phase cosmetic composition including an aqueous phase and an oily phase wherein the aqueous phase contains an emulsifying system comprising at least one surfactant selected from the group of cationic surfactants and at least one surfactant selected from the group of non-ionic surfactants, and wherein the total surfactant concentration is lower than 0.1%, by weight, based on the total weight of the composition.

8 Claims, No Drawings

TWO-PHASE COSMETIC COMPOSITION

FIELD OF THE INVENTION

The present invention relates to a two-phase cosmetic composition especially for the region of the eyes and face consisting of two phases, a lower aqueous phase comprising surfactants and a higher or oily phase.

The cosmetic composition according to this invention is particularly useful as a composition for removing makeup that removes two types of makeup: waterproof and non-waterproof.

BACKGROUND OF THE INVENTION

The principle for the operation of a two-phase makeup removing composition is based on the presence of the two above-mentioned phases, the purpose of the lower phase being to remove non-waterproof makeup and of the higher phase being to remove waterproof makeup.

When allowed to rest, the product shows the separation between the two phases and in order to act as simultaneously to remove the two different types of makeup, each one compatible with one of its bases, it is necessary to stir the product so that it becomes temporarily emulsified and the emulsion achieved in this way, which is a mixture of the two phases, manages to remove the two types of makeup satisfactorily.

The technical problem relating to achieving such a composition relies on the two principal factors which makes it necessary to develop a solution for the adequate performance of the product.

On the one hand, while the product must remain emulsified for sufficient time for the user to remove all her make up, on the other hand it should not cause any irritation since it is a product that may be applied to sensitive areas of the skin such as around the eyes and the face.

The time of emulsification or the period during which both phases remain "mixed together" (emulsified) is defined by the emulsifying system contained in the product, and emulsifiers or surfactants generally cause skin irritation. Therefore when the emulsifying system is configured so that the product remains emulsified for a long period, this tends to cause more irritation to the skin. If the emulsifying system is configured to cause little irritation the product tends to remain emulsified for a shorter period of time, obliging the user to interrupt the removal of the makeup, to put the top back on the flask and shake it again to obtain the two-phase emulsion.

The patent granted under number PI 8905734-1 teaches a cosmetic composition of the two-phase type that comprises a surfactant concentration in the range of 0.1 to 4% by weight, relative to the total weight of the composition. If it is considered that the weight ratio between the aqueous phase and the oily phase is from 30:70 to 60:40, it may be concluded that the concentration of the surfactant is from 0.33 to 0.16% by weight, relative to the weight of the aqueous phase.

The composition described in the above cited document presents the disadvantages of excessively irritating the skin and of remaining emulsified for an inadequate period.

Patent application PI 9603604-4 also filed in the name of the present applicant describes a two-phase cosmetic composition for the eyes and face, that comprises a minimum limit of 0.1% of the surfactant present in the aqueous phase, and the specification mentions the advantages derived from a generally low surfactant concentration.

In spite of being efficient, that composition still needs to be improved in order to minimize its property of skin irritation as well as to optimize the time that such a composition remains emulsified, in order to ensure that this time is closer to the time spent by the user in removing the makeup.

From patent application GB 2206048 it is known that a two-phase composition for removing makeup can contain a minimum concentration of dimethicone of 0.05% by weight based on the oily phase. However the term 'dimethicone' described there is deprived of the "copolyol" denomination, which clearly means that the 'dimethicone' is used in the composition proposed in that document with the function of a solvent or anything other than an emulsifier.

There is, therefore, a technical problem to be solved, namely, reducing the concentration of surfactants to a value below 0.1% in relation to the total weight of the composition in order to obtain a two-phase cosmetic composition which is less irritating to the skin but which remains emulsified for an ideal time.

OBJECTIVES OF THE INVENTION

It is therefore the purpose of the present invention to solve the technical problem of providing a cosmetic composition, in particular for the region of the eyes and the face, which provides low irritation due to an emulsifying system with low content of emulsifier and of specific classes, and which at the same time allows the ideal time for the emulsification.

SUMMARY OF THE INVENTION

The present invention refers to a two-phase cosmetic composition comprising an aqueous phase and an oily phase wherein the aqueous phase contains an emulsifying system comprising at least one surfactant selected from the group of cationic surfactants and at least one surfactant selected from the group of non-cationic surfactants and at least one surfactant selected from the group of non-ionic surfactants, and wherein the total concentration of surfactants is lower than 0.1% by weight, based on the total weight of the composition.

DETAILED DESCRIPTION OF THE INVENTION

After detailed studies it was surprisingly observed that a two-phase cosmetic composition containing an emulsifying system comprising surfactants in a total content lower than 0.1% with regard to the total weight of the composition is capable of remaining emulsified for an ideal time without causing irritation to the skin when an association of two groups of surfactants is used in the emulsifying system, the first of which is selected from non-ionic surfactants and the second one from cationic surfactants.

A cosmetic composition according to the invention is particularly useful as a makeup removing composition, primarily for the area of the eyes and face. Such a composition will normally comrpise a weight ratio from the aqueous phase to the oily phase in the range of 30:70 to 60:40, preferably 60:40, and the emulsifying system is preferably present in a proportion of about 0.02 to 0.09%, more preferably 0.060 to 0.065% by weight, based on the aqueous phase.

For the objectives of the present invention, and in the case of a two-phase makeup removing composition, the cationic surfactant used is preferably benzalkonium chloride and the non-ionic surfactant is preferably selected from the group including copolyol dimethicone, poloxamer or mixtures thereof.

The cosmetic composition defined herein also contains other conventional ingredients of this type of formulation and which can be easily identified by any specialist in this area depending on the specific objectives desired in each particular case.

However it must be pointed out that one of the advantages of the present invention when formulated as a makeup removing composition, is that it makes it unnecessary to use synthetic oils, especially palmitate or alkyl adipate in the oily phase, which are normal components of this type of composition. According to the present invention other cosmetic oils can be used such as isohexadecane with less oily characteristics, resulting in a product which is less oily to the touch.

The same happens in the absence of silicone oil, since the present invention enables the cyclomethicone/dimethicone system to be replaced simply by cyclomethicone due to the new emulsifying system adopted which further provides the advantages of a lower product cost as well as greater comfort for the user, since there is a different synergy between the new emulsifying system and cyclomethicone which brings softness to the skin, being neither sticky nor greasy.

Still according to a preferred embodiment of the invention, the composition also includes glycerin which allows the skin to be kept hydrated for prolonged periods of time, as much as up to five hours.

Furthermore, another advantage resulting from a two-phase composition based on this invention, and also concerning the reduced irritation aspect, is the fact that the compounds used result in a product with a final appearance that is cosmetically acceptable, allowing same to be formulated without colorants and perfumes.

The illustrative examples presented below will better describe the present invention However, the data given in the examples refer merely to some embodiments of the present invention, and should not be taken in any way to limit the scope thereof.

EXAMPLES

Formulations of two-phase makeup removers were prepared in accordance with the following chemical compositions (all the quantitative ranges are defined as wt %):

Formula 1:

| A) | Aqueous Phase: | | |
| --- | --- | --- | --- |
| | Demineralized Water | qs | Vehicle |
| | Propylene glycol | 2–10 | Moisturizer |
| | Glycerin | 2–10 | Moisturizer |
| | Sodium Chloride | 0.5–2.5 | Electrolyte |
| | Benzylic Alcohol | 0.1–1.0 | Preservative |
| | Benzalkonium chloride | 0.01–0.03 | Surfactant |
| | Copolyol Dimethicone | 0.01–0.03 | Emulsifier |
| | Poloxamer | 0.02–0.04 | Surfactant |
| | Potassium Phosphate | 0.1–0.3 | Buffer |
| | Sodium Phosphate | 0.7–0.9 | Buffer |
| B) | Oily phase: | | |
| | Cyclomethicone | 50–70 | Solvent |
| | Higher Aliphatic Hydrocarbon | 30–50 | Solvent |

Formula 2:

| A) | Aqueous Phase: | | |
| --- | --- | --- | --- |
| | Demineralized Water | qs | Vehicle |
| | Propylene glycol | 2–10 | Moisturizer |
| | Sodium Chloride | 0.5–2.5 | Electrolyte |
| | Benzylic Alcohol | 0.1–1.0 | Preservative |
| | Benzalkonium chloride | 0.01–0.03 | Surfactant |
| | Poloxamer | 0.02–0.04 | Surfactant |
| | Potassium Phosphate | 0.1–0.3 | Buffer |
| | Sodium Phosphate | 0.7–.09 | Buffer |
| B) | Oily phase: | | |
| | Cyclomethicone | 50–70 | Solvent |
| | Higher Aliphatic Hydrocarbon | 30–50 | Solvent |

Formula 3:

| A) | Aqueous Phase: | | |
| --- | --- | --- | --- |
| | Demineralized Water | Qs | Vehicle |
| | Propylene glycol | 2–10 | Moisturizer |
| | Sodium Chloride | 0.5–2.5 | Electrolyte |
| | Benzylic Alcohol | 0.1–1.0 | Preservative |
| | Benzalkonium chloride | 0.01–0.03 | Surfactant |
| | Copolyol Dimethicone | 0.01–0.03 | Emulsifier |
| | Potassium Phosphate | 0.1–0.3 | Buffer |
| | Sodium Phosphate | 0.7–0.9 | Buffer |
| B) | Oily phase: | | |
| | Cyclomethicone | 50–70 | Solvent |
| | Higher Aliphatic Hydrocarbon | 30–50 | Solvent |

Formula 4:

| A) | Aqueous Phase: | | |
| --- | --- | --- | --- |
| | Demineralized Water | Qs | Vehicle |
| | Propylene glycol | 2–10 | Moisturizer |
| | Sodium Chloride | 0.2–2.5 | Electrolyte |
| | Benzylic Alcohol | 0.1–1.0 | Preservative |
| | Benzalkonium chloride | 0.01–0.03 | Surfactant |
| | Copolyol Dimethicone | 0.01–0.03 | Emulsifier |
| | Poloxamer | 0.02–0.04 | Surfactant |
| | Potassium Phosphate | 0.1–0.03 | Buffer |
| | Sodium Phosphate | 0.7–0.9 | Buffer |
| B) | Oily phase: | | |
| | Cyclomethicone/ Dimethicone | 50–70 | Solvent |
| | Higher Aliphatic Hydrocarbon | 30–50 | Solvent |

Formula 5:

| A) | Aqueous Phase: | | |
| --- | --- | --- | --- |
| | Demineralized Water | Qs | Vehicle |
| | Propylene glycol | 2–10 | Moisturizer |
| | Sodium Chloride | 0.5–2.5 | Electrolyte |
| | Benzylic Alcohol | 0.1–1.0 | Preservative |
| | Benzalkonium chloride | 0.01–0.03 | Surfactant |
| | Copolyol Dimethicone | 0.01–0.03 | Emulsifier |
| | Poloxamer | 0.02–0.04 | Surfactant |
| | Potassium Phosphate | 0.1–0.3 | Buffer |
| | Sodium Phosphate | 0.7–0.9 | Buffer |

What is claimed is:

1. A two-phase cosmetic composition comprising an aqueous phase and an oily phase, wherein the aqueous phase contains an emulsifying system including at least one cationic surfactant and at least one non-ionic surfactant, and wherein a total concentration of all surfactants is lower than 0.1% in weight, based on a total weight of the composition.

2. A two-phase cosmetic composition according to claim 1, wherein the cationic surfactant is benzalkonium chloride.

3. A two-phase cosmetic composition according to claim 2, wherein the non-ionic surfactant is selected from the group consisting of copolyol dimethicone, poloxamer and mixtures thereof.

4. A composition according to claim 3, wherein the emulsifying system is present in a concentration in the range of from 0.060 to 0.065%, by weight, based on the aqueous phase.

5. A two-phase cosmetic composition according to claim 1, wherein the non-ionic surfactant is selected from the group consisting of copolyol dimethicone, poloxamer and mixtures thereof.

6. A composition according to claim 5, wherein the emulsifying system is present in a concentration in the range of from 0.060 to 0.065%, by weight, based on the aqueous phase.

7. A composition according to claim 2, wherein the emulsifying system is present in a concentration in the range of from 0.060 to 0.065%, by weight, based on the aqueous phase.

8. A composition according to claim 1, wherein the emulsifying system is present in a concentration in the range of from 0.060 to 0.065%, by weight, based on the aqueous phase.

* * * * *